US006982155B1

(12) United States Patent
Fukuda et al.

(10) Patent No.: US 6,982,155 B1
(45) Date of Patent: Jan. 3, 2006

(54) PROCESS FOR PRODUCING FATTY ACID LOWER ALCOHOL ESTER

(75) Inventors: Hideki Fukuda, Kobe (JP); Hideo Noda, Amagasaki (JP)

(73) Assignee: Kansai Chemical Engineering Co., Ltd., Hyogo (JP)

( * ) Notice: Subject to any disclaimer, the term of this patent is extended or adjusted under 35 U.S.C. 154(b) by 370 days.

(21) Appl. No.: 10/130,977

(22) PCT Filed: Nov. 20, 2000

(86) PCT No.: PCT/JP00/08185

§ 371 (c)(1),
(2), (4) Date: May 24, 2002

(87) PCT Pub. No.: WO01/38553

PCT Pub. Date: May 31, 2001

(30) Foreign Application Priority Data

Nov. 26, 1999 (JP) .................................. 11-336681

(51) Int. Cl.
*C12P 7/62* (2006.01)
(52) U.S. Cl. ...................... 435/135; 435/134; 554/161; 554/162; 554/167; 554/168
(58) Field of Classification Search ................ 554/161, 554/162, 167, 168; 435/134, 135
See application file for complete search history.

(56) References Cited

FOREIGN PATENT DOCUMENTS

| JP | (1989) 64-10994 A | 1/1989 |
|---|---|---|
| JP | (1989) 1-309689 A | 12/1989 |
| JP | (1993) 5-344896 A | 12/1993 |
| JP | (1994) 6-197777 A | 7/1994 |
| JP | (1999) 11-290078 A | 10/1999 |
| JP | (2000) 2000-270886 A | 10/2000 |

OTHER PUBLICATIONS

Shimada et al., JAOCS, vol. 76, No. 7, pp. 789-793, Jul. 1999.*
Kaieda et al., abstr. Biodiesel fuel production from plant oil catalyzed by Rhizopus oryzae lipase in a water-containing system without an organic solvent, vol. 42, p. 64, Oct. 1999.*
Nelson, Lloyd A. et al., "Lipase-Catalyzed Production of Biodiesel", *JAOCS*, 1996, pp. 1191-1195, vol. 73, No. 8.
Felix, Hansruedi, "Permeabilized Cells", *Analytical Biochemistry*, 1982, pp. 211-234, vol. 120.
Kanai, T. et al., "A novel heterologous gene expression system in *Saccharomyces cerevisiae* using the isocitrate lyase gene promoter from *Candida tropicalis*", *Appl. Microbiol. Biotechnol.*, 1996, pp. 759-765, vol. 44.

Takahashi, Shouji et al., "Extracellullar Production of Active *Rhizopus oryae* Lipase by *Saccharomyces cerevisiae*", *Journal of Fermentation and Bioengineering*, 1998, pp. 164-168, vol. 86, No. 2.
Shimada, Yuji et al., "Conversion of Vegetable Oil to Biodiesel Using Immobilized *Canadida antarctica* Lipase", *JAOCS*, 1999, pp. 789-793, vol. 76, No. 7.
Kaieda, Masaru et al., "Biodiesel Fuel Production from Plant Oil Catalyzed by *Rhizopus oryae* Lipase in a Water-Containing System without an Organic Solvent", *Journal of Bioscience and Bioengineering*, 1999, pp. 627-631, vol. 88, No. 6.
Beer, H. Dietmar et al., "Cloning, expression, characterization and role of the leader sequence of a lipase from *Rhizopous oryzae*", *Biochimica et Biophysica Acta*, 1998, pp. 173-180, vol. 1399.
Minning, Stefan et al., "Functional expression of *Rhizopus oryae* lipase in *Pichia pastoris*: high-level production and some properties", *Journal of Biotechnology*, 1998, pp. 147-156, vol. 66.
Liu, Yan et al., "Production of S-Lactoylglutathione by High Activity Whole Cell Biocatalysts Prepared by Permeabilization of Recombinant *Saccharomyces cerevisiae* with Alcohols", *Biotechnology and Bioengineering*, Jul. 5, 1999, pp. 54-60, vol. 64, No. 1.
Liu, Yan et al., "Production of Whole Cell Biocatalysts with High Activity by Treating Cell Membranes of a Recombinant Yeast: Effect of Treatment Conditions", *Kagaku Kougakukai Nenkai Kenkyu Happyou Kouen Youshisyuu*, Feb. 1999, p. 225, vol. $64^{th}$, *partial translation*.
Kaieda, Masaru et al., "Biodiesel Fuel Production from Plant Oil Catalyzed by *Rhizopus oryzae* Lipase in a Water-Containing System without an Organic Solvent", *Koso Kougaku Kenkyukai Kouenkai Kouen Youshisyuu* (1999) 42, p. 64.

* cited by examiner

Primary Examiner—Deborah D. Carr
(74) Attorney, Agent, or Firm—The Webb Law Firm, P.C.

(57) ABSTRACT

The present invention provides a method for producing a fatty acid ester inexpensively and efficiently by reacting a lipase or an intact mircroorganism containing a lipase, an oil and fat, and a linear lower alcohol in a system containing little or no solvent in the presence of water. The intact microorganism has not been treated with a solvent or the like, and is used as such, so that a fatty acid ester can be prepared in a simple manner. An oil and fat, a natural oil and fat such as a vegetable oil and fat, an animal oil and fat, as well as a waste oil thereof can be used. According to the method of the present invention, a reaction proceeds even in the presence of water, so that waste oils containing a large amount of water can be used as a raw material. Therefore, the waste oil to be dumped into the environment can be recycled, and a biodiesel fuel, which hardly pollutes the environment, can be provided at the same time.

6 Claims, 3 Drawing Sheets

SEQUENCE LISTING

<160> NUMBER OF SEQ ID NOS: 3

<210> SEQ ID NO 1
<211> LENGTH: 1104
<212> TYPE: DNA
<213> ORGANISM: Rhizopus oryzae IFO 4697

<400> SEQUENCE: 1

-continued

| | | |
|---|---|---|
| atg gtt cct gtt tct ggt aaa tct gga tct tcc aac acc gcc gtc tct<br>Met Val Pro Val Ser Gly Lys Ser Gly Ser Ser Asn Thr Ala Val Ser<br>-98        -95             -90             -85 | | 48 |
| gca tct gac aat gct gcc ctc cct cct ctc atc tcc agc cgt tgt gct<br>Ala Ser Asp Asn Ala Ala Leu Pro Pro Leu Ile Ser Ser Arg Cys Ala<br>      -80             -75             -70 | | 96 |
| cct cct tct aac aag gga agt aaa agc gat ctc caa gct gaa cct tac<br>Pro Pro Ser Asn Lys Gly Ser Lys Ser Asp Leu Gln Ala Glu Pro Tyr<br>      -65             -60             -55 | | 144 |
| aac atg caa aag aat aca gaa tgg tat gag tcc cat ggt ggc aac ctg<br>Asn Met Gln Lys Asn Thr Glu Trp Tyr Glu Ser His Gly Gly Asn Leu<br>-50             -45             -40             -35 | | 192 |
| aca tcc atc gga aag cgt gat gac aac ttg gtt ggt ggc atg act ttg<br>Thr Ser Ile Gly Lys Arg Asp Asp Asn Leu Val Gly Gly Met Thr Leu<br>           -30             -25             -20 | | 240 |
| gac tta ccc agc gat gct cct cct atc agc ctc tct agc tct acc aac<br>Asp Leu Pro Ser Asp Ala Pro Pro Ile Ser Leu Ser Ser Ser Thr Asn<br>      -15             -10             -5 | | 288 |
| agc gcc tct gat ggt ggt aag gtt gtt gct gct act act gct cag atc<br>Ser Ala Ser Asp Gly Gly Lys Val Val Ala Ala Thr Thr Ala Gln Ile<br>      -1   1               5               10 | | 336 |
| caa gag ttc acc aag tat gct ggt atc gct gcc act gcc tac tgt cgt<br>Gln Glu Phe Thr Lys Tyr Ala Gly Ile Ala Ala Thr Ala Tyr Cys Arg<br>15             20             25             30 | | 384 |
| tct gtt gtc cct ggt aac aag tgg gat tgt gtc caa tgt caa aag tgg<br>Ser Val Val Pro Gly Asn Lys Trp Asp Cys Val Gln Cys Gln Lys Trp<br>           35             40             45 | | 432 |
| gtt cct gat ggc aag atc atc act acc ttt acc tcc ttg ctt tcc gat<br>Val Pro Asp Gly Lys Ile Ile Thr Thr Phe Thr Ser Leu Leu Ser Asp<br>           50             55             60 | | 480 |
| aca aat ggt tac gtc ttg aga agt gat aaa caa aag acc att tat ctt<br>Thr Asn Gly Tyr Val Leu Arg Ser Asp Lys Gln Lys Thr Ile Tyr Leu<br>           65             70             75 | | 528 |
| gtt ttc cgt ggt acc aac tcc ttc aga agt gcc atc act gat atc gtc<br>Val Phe Arg Gly Thr Asn Ser Phe Arg Ser Ala Ile Thr Asp Ile Val<br>80             85             90 | | 576 |
| ttc aac ttt tct gac tac aag cct gtc aag ggc gcc aaa gtt cat gct<br>Phe Asn Phe Ser Asp Tyr Lys Pro Val Lys Gly Ala Lys Val His Ala<br>95             100           105          110 | | 624 |
| ggt ttc ctt tcc tct tat gag caa gtt gtc aat gac tat ttc cct gtc<br>Gly Phe Leu Ser Ser Tyr Glu Gln Val Val Asn Asp Tyr Phe Pro Val<br>             115           120          125 | | 672 |
| gtc caa gaa caa ttg acc gcc cac cct act tat aag gtc atc gtt acc<br>Val Gln Glu Gln Leu Thr Ala His Pro Thr Tyr Lys Val Ile Val Thr<br>             130           135          140 | | 720 |
| ggt cac tca ctc ggt ggt gca caa gct ttg ctt gcc ggt atg gat ctc<br>Gly His Ser Leu Gly Gly Ala Gln Ala Leu Leu Ala Gly Met Asp Leu<br>          145             150          155 | | 768 |
| tac caa cgt gaa cca aga ttg tct ccc aag aat ttg agc atc ttc act<br>Tyr Gln Arg Glu Pro Arg Leu Ser Pro Lys Asn Leu Ser Ile Phe Thr<br>160          165           170 | | 816 |
| gtc ggt ggt cct cgt gtt ggt aac ccc acc ttt gct tac tat gtt gaa<br>Val Gly Gly Pro Arg Val Gly Asn Pro Thr Phe Ala Tyr Tyr Val Glu<br>175           180           185          190 | | 864 |
| tcc acc ggt atc cct ttc caa cgt acc gtt cac aag aga gat atc gtt<br>Ser Thr Gly Ile Pro Phe Gln Arg Thr Val His Lys Arg Asp Ile Val<br>             195           200          205 | | 912 |
| cct cac gtt cct cct caa tcc ttc gga ttc ctt cat ccc ggt gtt gaa<br>Pro His Val Pro Pro Gln Ser Phe Gly Phe Leu His Pro Gly Val Glu | | 960 |

-continued

```
                  210              215              220
tct tgg atc aag tct ggt act tcc aac gtt caa atc tgt act tct gaa    1008
Ser Trp Ile Lys Ser Gly Thr Ser Asn Val Gln Ile Cys Thr Ser Glu
        225              230              235 att gaa acc aag gat tgc agt aac tct atc gtt cct ttc acc tct atc    1056
Ile Glu Thr Lys Asp Cys Ser Asn Ser Ile Val Pro Phe Thr Ser Ile
    240              245              250 ctt gac cac ttg agt tac ttt gat atc aac gaa gga agc tgt ttg taa    1104
Leu Asp His Leu Ser Tyr Phe Asp Ile Asn Glu Gly Ser Cys Leu
255              260              265              269
```

<210> SEQ ID NO 2
<211> LENGTH: 40
<212> TYPE: DNA
<213> ORGANISM: Artificial Sequence
<220> FEATURE:
<223> OTHER INFORMATION: Ics, used as primer in PCR

<400> SEQUENCE: 2
ctccggatcc atggttcctg tttctggtaa atctggatct                40

<210> SEQ ID NO 3
<211> LENGTH: 25
<212> TYPE: DNA
<213> ORGANISM: Artificial Sequence
<220> FEATURE:
<223> OTHER INFORMATION: ROLrvSalI, used as primer in PCR

<400> SEQUENCE: 3
cgatgtcgac ttacaaacag cttcc                                25

PROCESS FOR PRODUCING FATTY ACID LOWER ALCOHOL ESTER

BACKGROUND OF THE INVENTION

1. Field of the Invention

The present invention relates to a method for producing a fatty acid lower alcohol ester employing a lipase, and a microorganism containing a lipase suitable for the method.

2. Description of the Prior Art

In general, fossil fuels typified by petroleum and light oil are used as fuels for automobiles. These fossil fuels, especially, light oil used in diesel automobiles contain a large amount of nitrogen compounds and sulfur compounds, so that a large amount of gas such as $CO_2$, NOx, and SOx are exhausted from automobiles such as diesel automobiles. Since these exhaust gases cause global warming and environmental pollution, reduction of the exhaust amount is an issue to be solved urgently.

As an alternative fuel to fossil fuels such as light oil, there are high expectations in so-called biodiesel fuel, which uses oils and fats produced by naturally occuring plants, animals, fishes or microorganisms. Among these oils and fats, the oils and fats used for food production are often dumped into the environment and cause environmental problems. Therefore, expectations in biodiesel fuel made from waste oil are particularly high in view of prevention of air pollution and effective utilization of waste oil.

Fatty acid lower alcohol esters are preferably used as biodiesel fuels. In order to produce fatty acid lower alcohol esters from oils and fats, a technique for separating an oil and fat into the glycerin and a fatty acid constituting it, and then producing an ester from an alcohol and a fatty acid is required. As one of the methods, a variety of research on the production of fatty acid esters using a lipase is conducted.

However, the method used at present is to dissolve an oil and fat in a solvent (e.g., hexane, etc.) in order to react the oil and fat using a lipase in the presence of an alcohol. In this method, it is necessary to separate fatty acid esters from the solvent, which requires an operation for collecting the solvent, and therefore the process becomes complicated and the cost increases. In addition to these disadvantages, there is the danger of explosion. For these reasons, it is attempted to develop the method in a solvent-free system.

An experimental example using a solvent-free system is described in JAOCS vol. 73, pp. 1191–1195 (1996). According to this experiment, when branched alcohols such as isopropanol, isobutanol, and 2-butanol are used, a fatty acid ester can be obtained in a ratio of 90% or more. However, when industrially used inexpensive alcohols such as methanol and ethanol are used, the fatty acid esterification reaction hardly proceeds. Thus, at present, a method for producing non-energy consumption type biodiesel (fatty acid ester) using an inexpensive alcohol in a solvent-free system has not been established yet.

On the other hand, in a synthetic reaction of a fatty acid ester using a lipase, a method using a lipase which is isolated and immobilized has been most commonly examined. However, this method has the problem of taking much time for the isolation and immobilization of the lipase.

Furthermore, it is also under examination that a microorganism itself is used. The need of considering the permeability of the cell membrane has been pointed out, so that a treatment of the microorganism with a solvent such as an alcohol is under examination (for example, see Felix et al., Anal. Biochem. 120: 211–234 (1982)). This solvent treatment also requires time and cost for the treatment and the collection of the solvent, and has the problem of the danger of explosion.

Furthermore, a transesterification using a lipase is carried out in a nonaqueous system in view of hydrolysis of a produced fatty acid ester. In particular, when waste oil containing a large amount of water is used, the progress of the reaction is inhibited. Therefore, facilities for removing water are necessary, which increases the cost. A method for producing a fatty acid lower alcohol ester in the presence of water is described in Japanese Laid-Open Patent Publication No. 64-10994. However, in this method, a special enzyme has to be used, and isolation of the enzyme takes time and costs, so that this method has not been put to practical use.

Thus, in the transesterification using a lipase, none of the above problems has been solved so that there is a demand for a method for producing a fatty acid ester more efficiently.

SUMMARY OF THE INVENTION

The present invention is carried out to solve the above problems, and provides a method for producing a fatty acid ester efficiently in a system containing little or no solvent and in the presence of water, without any treatment of a lipase and a microorganism containing a lipase using an inexpensive alcohol such as methanol and ethanol for improvement of the cell membrane permeability or the like (i.e., using an intact microorganism). Thus, the present invention solves the above problems simultaneously.

The present invention provides a method for producing a fatty acid ester, which comprises reacting a lipase or an intact microorganism containing a lipase with an oil and fat and a linear lower alcohol in a system containing little or no solvent in the presence of water.

In a preferable embodiment, the intact microorganism is immobilized in a porous carrier.

In a preferable embodiment, the microorganism can express a recombinant lipase that does not have a functional sequence involved in secretion.

In a preferable embodiment, the water is contained in an amount of 0.3 wt % or more in a reaction mixture.

In a preferable embodiment, the oil and fat is a vegetable oil and fat, an animal oil and fat, a fish oil, an oil and fat produced by a microorganism, a mixture of these oils and fats, or a waste oil thereof.

In another preferable embodiment, the linear lower alcohol is methanol, and is adjusted so that the methanol is contained in an amount of 30 wt % or less with respect to a total amount of the methanol and the water.

In a preferable embodiment, the linear lower alcohol is added stepwise.

The present invention further provides a recombinant microorganism, which has a DNA sequence capable of expressing a lipase that does not have a functional sequence involved in secretion, and can contain the lipase in its cell.

DETAILED DESCRIPTION OF THE INVENTION

The present invention is characterized in that when synthesizing a fatty acid ester by reacting an oil and fat with a linear lower alcohol and a lipase in a system containing little or no solvent in the presence of water, an intact microorganism is used as the lipase. The present invention is also characterized in that the microorganism can express a recombinant lipase that does not have a functional sequence involved in secretion, that is, the microorganism accumulates a lipase within a cell.

In the specification, a "lipase" means an enzyme having an ability to degrade the glyceride into glycerin or a partial glyceride and a fatty acid.

An "intact microorganism" means a microorganism that has not been subjected to any treatment for improving the permeability of the cell membrane (e.g., solvent treatment). Microorganisms that are simply dried are also intact microorganisms.

A "linear lower alcohol" refers to a linear alcohol having 1 to 8 carbon atoms. In particular, methanol, ethanol or propanol is preferable.

A "system containing no solvent" refers to a system that does not contain a solvent for dissolving oils and fats, and a linear lower alcohol used for esterification reaction is not a solvent referred to in the specification of the present invention.

A "system containing little solvent" refers to a system to which a solvent is added supplementarily to dissolve oils and fats in a linear lower alcohol used for esterification. Even if oils and fats are not dissolved completely in a linear lower alcohol, the reaction proceeds, so that it is not necessary to add a solvent. By adding a solvent, oils and fats are dissolved, so that it is possible to increase the reaction rate.

(Microorganism)

One of the features of the present invention is to use "intact microorganisms". Any microorganisms can be used, as long as they produce a lipase. In view of recycling, immobilized microorganisms are preferable. As a result of using intact microorganisms, a treatment with a solvent (e.g., alcohol, acetone, chloroform, etc.) that is conventionally used for the purpose of improving the permeability of the cell membrane can be eliminated, so that facilities for collecting the solvent or facilities for preventing explosion are unnecessary, which reduces the production cost significantly.

A lipase may be 1,3-specific or nonspecific. In view of production of fatty acid esters, a nonspecific lipase is preferable. Any microorganisms can be used, as long as they produce such lipase. For example, filamentous fungus, bacteria, yeasts or the like can be used.

As filamentous fungus, microorganisms belonging to Genus *Aspergillus, Galactomyces, Geotricum, Mucor, Phycomyces, Rhizomucor, Penicillium, Rhizopus* or the like can be used.

As bacteria, microorganisms belonging to Genus *Pseudomonas, Alkaligenes* or the like can be used.

As yeasts, microorganisms belonging to Genus *Candida, Cryptococcus, Pichia, Rhodotorula, Yarrowia* or the like can be used.

It is more preferable that the above microorganisms are heat resistant, because the reaction temperature can be increased.

It is preferable to use a recombinant microorganism to which a lipase gene is introduced. It is preferable that this recombinant microorganism does not allow a lipase to be secreted from the microorganism. Therefore, it is preferable to use a microorganism that can express a recombinant lipase that does not have a functional sequence involved in secretion. Herein, a "functional sequence involved in secretion" refers to a so-called presequence (signal sequence), and "does not have a functional sequence involved in secretion" includes all variations of sequences that does not cause secretion, such as the following cases: whole presequences (signal sequences) are deleted; a part of the presequences are deleted so that secretion does not occur; and a presequence is destroyed (e.g., substitution, deletion, or addition, etc. of amino acids) so that the secretion does not occur.

Such a gene encoding a lipase that does not have a functional sequence involved in secretion can be produced based on a known lipase gene, using a gene recombination technique that is routinely used by those skilled in the art. It is conventionally believed that a lipase is secreted and then expressed functionally, but the inventors of the present invention found out for the first time that free lipase (i.e., lipase having no presequence) is expressed and accumulated within the cell, and that even if the lipase is present within the cell of a microorganism, the lipase within the cell can participate in fatty acid alcohol ester synthesis without any treatment of the microorganism.

It is preferable that the microorganism is immobilized in view of recycling. Immobilization can be performed by a suitable method selected by those skilled in the art as appropriate, depending on the microorganism. For example, an entrapment method, a physical adsorption method, a method of adsorbing or attaching to a carrier or the like can be used. The method of adsorbing or attaching a microorganism to a carrier is preferable, because it is easy to immobilize the microorganism.

In the present invention, a "carrier" refers to a substance to which a microorganism can be immobilized, preferably a substance that is insoluble in water or a specific solvent. As the material of the carrier used in the present invention, foams or resins such as polyvinyl alcohol, polyurethane foam, polystyrene foam, polyacrylamide, a polyvinyl formal resin porous material, silicone foam, a cellulose porous material, and foam ceramics are preferable. The size of the opening of the porous material or the foam depends on the microorganism to be immobilized. The size enough for a cell to enter and grow therein is suitable. In the case of bacteria such as *E. coli* and *Bacillus subtilis*, a size of about 10 $\mu$m to about 500 $\mu$m is preferable. In the case of filamentous funguses, yeasts or the like, a size of about 50 $\mu$m to about 1,000 $\mu$m is preferable, but the size is not limited thereto.

There is no limitation regarding the shape of the carrier. In view of the strength of the carrier, the cultivation efficiency or the like, spherical or cubical shapes are preferable. A preferable size is 2 mm to 50 mm in diameter for a spherical carrier, and 2 mm to 50 mm in length of the side for a cubical carrier.

As described above, the microorganism is immobilized simply by mixing the microorganism to be cultured with the carrier, and can be used without any treatment with acetone, alcohol or the like, or after being dried (that is, used as an intact immobilized microorganism).

The thus obtained intact immobilized microorganism is used for a reaction while being suspended, or is filled in a column or the like to be used as a so-called bioreactor, and can be repeatedly used continuously or by batch.

(Enzyme)

In the present invention, an enzyme (lipase) itself can be used. As the lipase, a lipase derived from the above-described microorganisms can be used, and a commercially available lipase also can be used. For example, trade name Lilipase A-10FG (derived from *Rhizopus Japonicas*), trade name SM Enzyme (derived from *Serratia marcescens*), trade name Lipase P, etc. manufactured by Nagase ChemteX Corporation; trade name Lipase F (derived from *Rhizopus oryzae*), trade name Lipase L (derived from *Candida lipolytica*), etc. manufactured by Amano Pharmaceutical Co., Ltd.; and Lipase-OF (derived from *Candida rugosa*) manufactured by Meito Sangyo Co., Ltd. can be used.

For the carrier, the above-described materials and shapes can be used. In the case of porous carriers, the opening thereof may not necessarily have the above-described size, and can have a size of 10 $\mu$m or less.

(Oil and Fat)

As the oil and fat, an oil and fat containing a large amount of glyceride, especially triglyceride, is preferable. As the oil and fat, vegetable oils and fats, animal oils and fats, fish oils, oils and fats produced by microorganisms, a mixture of these oils and fats, or waste oils thereof are used preferably. Examples of vegetable oils and fats include soybean oil, rape seed oil, palm oil, and olive oil. Examples of animal oils and fats include beef tallow, lard, sperm oil, and mutton tallow. Examples of fish oils include sardine oil, tuna oil, and squid oil. Examples of the oils and fat produced by microorganisms include oils and fats produced by microorganisms belonging to *Mortierella, Schizochytrium* or the like. In the method of the present invention, there is no problem even if water is contained in the reaction mixture. Therefore, a waste oil containing a large amount of water is one of the preferable raw materials.

(Ester Synthesis in the Presence of Water)

In the present invention, a reaction for synthesizing a fatty acid linear lower alcohol ester is performed in the presence of water. In general, it was believed that in a reaction for synthesizing a fatty acid linear lower alcohol ester using a lipase, water content was not preferable because an esterolytic reaction occurs.

On the other hand, in order to synthesize a fatty acid linear lower alcohol ester from triglyceride (which may be abbreviated as TG in the following) of the oils and fats and a linear lower alcohol most efficiently, it is theoretically necessary to add 3 mols of the linear lower alcohol with respect to 1 mol of TG. However, a certain concentration or more of the linear lower alcohol tends to inhibit or inactivate a lipase or a lipase within the microorganism.

The inventors of the present invention have studied to solve the problems simultaneously, and consequently found out that the above-described two problems can be solved at the same time by performing a reaction for synthesizing a fatty acid linear lower alcohol ester in the presence of water, using a lipase or an intact microorganism. In other words, the inventors of the present invention found out that inactivation or irreversible inactivation of a lipase can be prevented by adding water, and the synthesized fatty acid ester is not degraded even in the presence of water. As a result, a fatty acid ester is synthesized efficiently. Furthermore, it was also found out that a fatty acid ester is synthesized efficiently by stepwise addition of alcohol in the presence of water.

It is preferable that water is contained in an amount of 0.3 wt % or more with respect to the total amount of the reaction mixture, more preferably about 1 wt % to about 50 wt %, and even more preferably about 3 wt % to about 30 wt %.

When a reaction is performed by adding water, the preferable range of the concentration of the linear lower alcohol varies depending on the kind of alcohol used, but any concentrations can be used, as long as it does not cause inhibition due to the alcohol. In the case of methanol, a concentration of 30 wt % or less with respect to the total amount of the methanol and the water is preferable. A concentration of 25 wt % or less is more preferable and a concentration of 20 wt % or less is even more preferable. In this case, even if 3 mols or more of the linear lower alcohol is present with respect to 1 mol of an oil and fat, the lipase within the microorganism is not inhibited nor inactivated. Therefore, the microorganism can be recycled.

The water and the linear lower alcohol can be added separately, or can be formed into an aqueous solution having a suitable concentration and then added to an oil and fat (e.g., TG).

In the present invention, synthesis of fatty acid esters can be performed continuously by adding a linear lower alcohol to a reaction mixture, collecting a reaction product while maintaining the alcohol at the appropriate concentration, and separating a resultant fatty acid ester and glycerin (e.g., separation by standing).

Furthermore, as another method, the linear lower alcohol can be subjected to stepwise addition in order to avoid the inhibition due to the linear lower alcohol. In other words, the linear lower alcohol is added such that the concentration is lower than the lipase inhibition concentration. The "lipase inhibition concentration" refers to a concentration at which the activation of the lipase in the microorganism is inhibited, or the lipase is inactivated irreversibly.

There is no particular limitation regarding the method for the stepwise addition of the linear lower alcohol. A batch-wise operation can be used, or a continuous operation can be used. In the case of a batchwise operation, the following method (multistage operation) can be used: A linear lower alcohol is allowed to react at a concentration lower than the lipase inhibition concentration, and then the linear lower alcohol is added thereto so that the concentration is lower than the lipase inhibition concentration, and further a trans-esterification is proceeded. Depending on the concentration of the linear lower alcohol, a reaction can be finished in two batches (two-stage reaction), or it can be finished in three batches (three stages) or more. For example, when using an intact immobilized microorganism and using methanol as the linear lower alcohol, it seems that the lipase is inhibited when the methanol amount is about 2 mols with respect to one mol of TG (see Example 1). Therefore, it is necessary to use methanol at a lower concentration. For example, first, the first stage reaction is performed by adding one mol of methanol with respect to one mol of TG. After the first stage reaction, the second stage reaction is performed by further adding one mol of methanol with respect to one mol of TG. After the second stage reaction is finished, the third stage reaction is performed by further adding one mol of methanol with respect to one mol of TG. Thus, the reaction is completed.

In another embodiment of stepwise addition, the linear lower alcohol can be dropped so that the concentration of the linear lower alcohol is constantly one mol or less with respect to one mol of TG, while monitoring the amount of the produced fatty acid lower alcohol ester or the amount of the consumed alcohol.

Since the lipase inhibition can be avoided in the presence of a fatty acid ester, a pre-mixed solution of a fatty acid ester with a linear lower alcohol can be added stepwise. The stepwise addition can be performed in a batchwise operation or a continuous operation. The fatty acid ester to be added may be the same as the fatty acid ester produced by reacting an oil and fat with the linear lower alcohol, or may be different. The fatty acid ester can be added so that the amount thereof at the start of the reaction is 5 wt % to 80 wt %, preferably 10 wt % to 80 wt %, more preferably 20 wt % to 70 wt %, and most preferably 30 wt % to 50 wt % of the reaction mixture. Since a fatty acid ester is newly produced by the ester synthesis reaction, it is preferred that an amount of the fatty acid ester to be added is smaller within the range that can avoid the inhibition.

The transesterification using an oil and fat, a linear lower alcohol, and an intact microorganism is performed generally at about 5° C. to about 80° C., preferably at about 15° C. to about 50° C., and more preferably at about 25° C. to about 45° C. The reaction temperature can be determined, depending on the microorganism used, and for example, when a heat resistant microorganism is used, a reaction can be performed at a relatively high temperature.

The reaction time can be determined depending on the composition of the oil and fat and the linear lower alcohol, and the enzyme amount.

After the reaction, the produced fatty acid ester is separated from glycerin and unreacted glyceride by a commonly used separating operation such as standing, centrifugation, membrane separation, molecular distillation and superfractionation, and then collected.

EXAMPLES

Hereinafter, the present invention will be described by way of examples, but the present invention is not limited to these examples.

(Preparation of Intact Immobilized Microorganisms and Solvent-Treated Microorganisms)

*Rhizopus oryzae* IFO 4697 was used as a lipase-producing microorganism. First, 39 g/l of potato dextrose agar (manufactured by Difco) and 20 g/l of agar (manufactured by Difco) were added to distilled water at 80° C. or more and dissolved with stirring, and the pH was adjusted to 5.5. Then, the mixture was added to a test tube in an amount of 5 ml for each, and was sterilized in an autoclave at 121° C. for 20 min to produce a slant. Microorganism cells were inoculated into this slant and cultured at 30° C. for 70 hours.

Then, 150 pieces of polyurethane foam with 6 mm cube (manufactured by Bridgestone Corporation: format HR-50: hereinafter, referred to as BSP) were placed in 100 ml of a medium having the following composition:

| | | |
|---|---|---|
| Glucose | 3 g/l | |
| Polypeptone | 70 g/l | |
| $NaNO_3$ | 1 g/l | |
| $MgSO_4 \cdot 7H_2O$ | 0.5 g/l | |
| $KH_2PO_4$ | 1 g/l | |
| pH | 5.6 | |

After the BSPs were sufficiently immersed in the medium, the BSPs were placed in a 500 ml Sakaguchi flask, and 30 g/l of oleic acid was added thereto and the mixture was sterilized in an autoclave at 121° C. for 20 min.

After the sterilization, spores in an amount corresponding to one slant described above were inoculated into 100 ml of the liquid medium that was cooled to 35° C., and were cultured at 35° C. for 90 hours with shaking at an amplitude of 70 mm and a shaking speed of 150 rpm. After the cultivation, the cells immobilized on the BSPs (hereinafter, referred to as "BSP-immobilized cells") were collected by filtration and washed with water.

The water was removed from the obtained BSP-immobilized cells within an extent that the cells were not removed, and dried at room temperature for 48 hours to obtain intact immobilized microorganisms. On the other hand, the BSP-immobilized cells were treated with methanol, ethanol, acetone, and isopropyl alcohol at 30° C. for 30 minutes, 60 minutes, and 120 minutes, and thus solvent-treated immobilized microorganisms were prepared.

Example 1

First, 1 g of water was added to each of 10 g of a mixture of 9.65 g of soybean oil and 0.35 g of methanol (molar ratio of 1:1) and 10 g of a mixture of 9.32 g of soybean oil and 0.68 g of methanol (molar ratio of 1:2) to prepare reaction mixtures. Then, 50 pieces of intact immobilized microorganisms or 50 pieces of solvent-treated immobilized microorganisms were added to these reaction mixtures, and allowed to react for 20 hours at 30° C. with shaking at 130 rpm. After the reaction, the produced fatty acid ester was quantified by gas chromatography (GC). GC was performed using tricaprylin as the internal standard, under the following conditions.

GC conditions:
Column: DB-5 (J&W Scientific, 10 m×25 mm)
Initial column temperature: 150° C. (0.5 min)
Temperature increase rate: 10° C./min
Final temperature: 300° C. (three minutes)
Injector temperature: 245° C.
Detector temperature: 320° C.
Carrier gas: helium (2.5 cm/min)
Split ratio: 1/100

The results are shown in Table 1. In Table 1, the conversion ratio means a conversion ratio of methanol into methyl ester.

TABLE 1

| | Microorganism | Treatment time (min) | | |
|---|---|---|---|---|
| Soybean oil/ | treatment | 30 | 60 | 120 |
| MeOH | solvent | Conversion rate (%) | | |
| molar ratio = 1:2 | no treatment | 81 | 81 | 81 |
| | methanol | 10 | 3 | 0 |
| | ethanol | 50 | 20 | 8 |
| | acetone | 80 | 62 | 30 |
| | iso-PrOH | 69 | 65 | 41 |
| molar ratio = 1:1 | no treatment | 100 | 100 | 100 |
| | methanol | 5 | 5 | 5 |
| | ethanol | 48 | 30 | 12 |
| | acetone | 80 | 64 | 43 |
| | iso-PrOH | 75 | 70 | 54 | iso-PrOH represents isopropyl alcohol.

These results show that when the soybean oil and methanol were added in a molar ratio of 1:1, the reaction proceeded at the rate of 100%, whereas when the soybean oil and methanol were added in a molar ratio of 1:2, the ester synthesis reaction did not proceed at the rate of 100% and the lipase activity was inhibited by about 20%. Furthermore, in the treatment with methanol, the lipase within the immobilized microorganism was almost all inactivated, and in the treatment with ethanol, the lipase activity was reduced to about 50%. In the treatments with acetone and isopropyl alcohol, the lipase activities were reduced as the treatment time increased. These results indicate that even if the lipase-producing microorganism has not been treated with any solvent and only has been dried, the microorganism has a sufficient lipase activity (fatty acid lower alcohol ester synthesis activitiy).

Example 2

First, 10 g of a mixture of 9.65 g of soybean oil and 0.35 g of methanol (molar ratio of 1:1) was prepared, and water in the amount shown in Table 2 was added thereto to prepare reaction mixtures. Then, each 50 pieces of intact immobilized microorganisms, acetone-treated immobilized microorganisms, or isopropyl alcohol-treated immobilized microorganisms were added to the reaction mixtures, and allowed to react for one day at 30° C. with shaking at 130 oscillations per min. Then, 0.31 g of methanol was added to the reaction mixtures, and allowed to react for further 24 hours (Day 2). Again 0.31 g of methanol was added thereto and allowed to react for one day (Day 3). Thereafter, a reaction was further performed for 3 days (thus a total of 6 days). The results are shown in Table 2. The conversion ratio in Table 2 is represented by the methyl esterification ratio of the fatty acid contained in the soybean oil.

TABLE 2

| Immobilized microorganism | Water (g) | Day 1 | Day 2 | Day 3 | Day 6 |
|---|---|---|---|---|---|
| intact (no treatment) | 0.3 | 19.2 | 25.8 | 46.1 | 69 |
|  | 1.0 | 32.9 | 65.3 | 92.1 | 97.1 |
|  | 3.0 | 30.5 | 66.8 | 98.0 | 98.8 |
| acetone treatment | 1.0 | 13.3 | 22.7 | 29.9 | 41.2 |
| iso-PrOH treatment | 1.0 | 15.2 | 31.2 | 39.9 | 51.8 |

These results indicate that even if about 3 to 30 wt % of water content was present, in the intact immobilized microorganisms, an ester synthesis reaction proceeded with substantially theoretical values. On the other hand, in the solvent-treated immobilized microorganism that has been subjected to a conventionally required solvent treatment such as an acetone treatment or an isopropyl alcohol treatment, the activity was not stabilized, and the reaction was much inferior to that in the intact immobilized microorganisms.

Example 3

A microorganism that can express a recombinant lipase that does not have a functional sequence involved in secretion was prepared.

Figure 1:
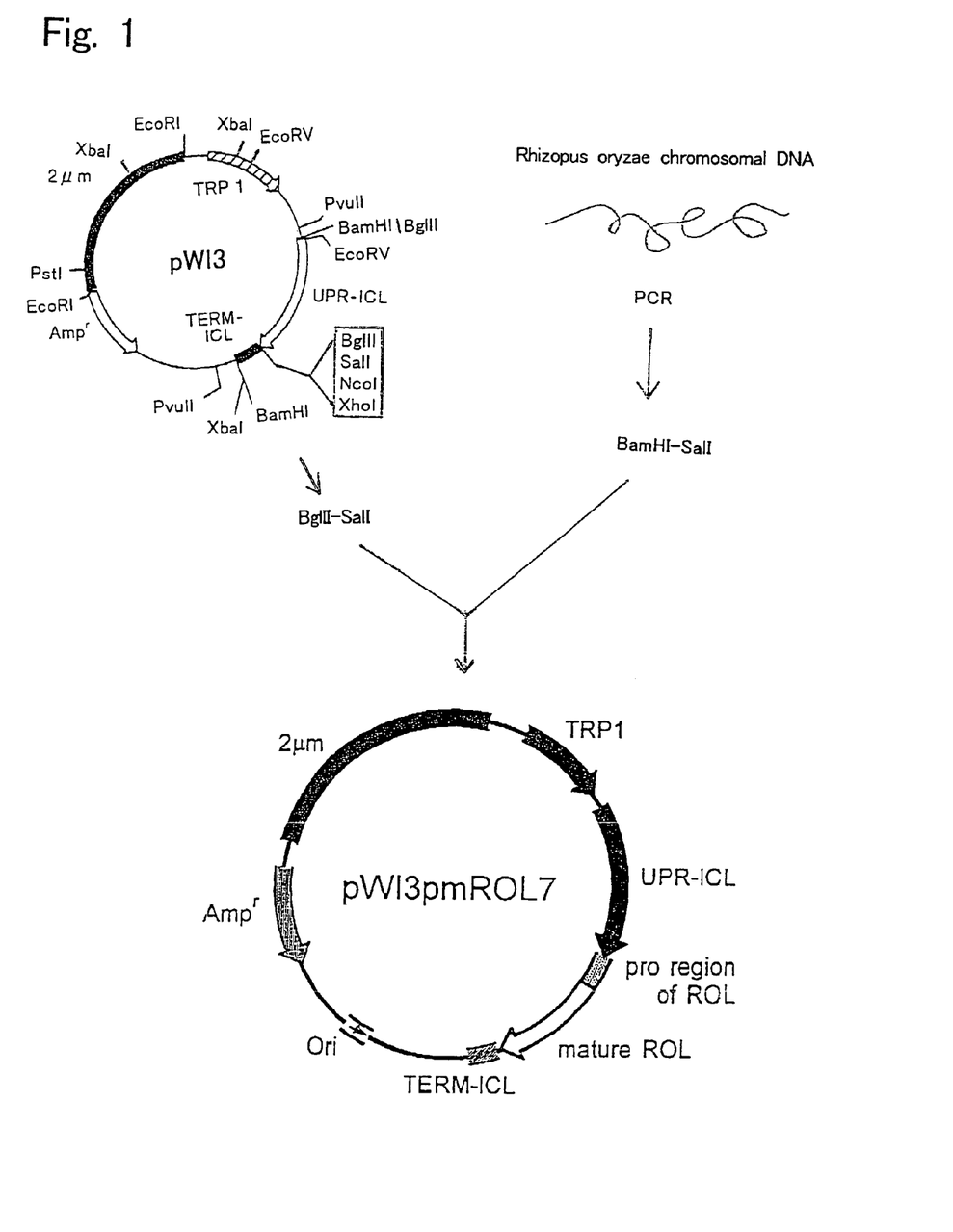
FIG. 1 is a schematic diagram showing construction of plasmid pWI3pmROL7 having a gene encoding a lipase which is accumulated within a cell, by using plasmid pWI3 as the starting material.

Plasmid pWI3 was used as the starting vector for producing a plasmid containing a DNA sequence encoding a recombinant lipase that does not have a functional sequence involved in secretion. A method for producing plasmid pWI3 is described in Kanai T. et al., Appl. Microbiol. Biotechnol. 1996, 44 (6), 759–765. The restriction enzyme map of plasmid pWI3 is shown in FIG. 1.

First, a chromosome of R. oryzae IFO 4697 was prepared by a conventional method. A lipase (ROL) gene derived from R. oryzae was obtained by amplification from this chromosomal DNA by PCR method using pfuTurbo polymerase (manufactured by Stratagene; #600250). In PCR, Ics (5'-ctccggatccatggttcctgtttctggtaaatctggatct-3': Sequence ID No: 2) and ROLrvSalI (5'-cgatgtcgacttacaaacagcttcc-3': Sequence ID No: 3) were used as primers. A ROL gene amplified using these two synthesized oligonucleotides has no gene sequence encoding a presequence (secretion signal peptide) and has a gene sequence including both a prosequence and a matured protein region. This sequence is shown in Sequence ID No: 1.

The sequence (ROL) obtained by the PCR amplification was digested by the restriction enzymes BamHI and SalI to purify a BamHI-SalI fragment of the ROL.

On the other hand, the plasmid pWI3 was digested by BglII and SalI, and then mixed with the BglII-SalI fragment of the ROL and connected thereto. It was confirmed that the ROL gene was appropriately inserted. The obtained plasmid was named pWI3 pmROL7 (see FIG. 1).

The plasmid pWI3 pmROL7 was transformed into yeast Saccharomyces cerevisiae MT8-1 (MATa ura3-1 trp1-1 ade2-1 leu2-3,112 his3) by the lithium acetate method, and a transformant was selected on a SD-W selection medium agar plate (2% glucose, 0.67 yeast nitrogen base w/o amino acids, 0.003% leucine, 0.002% adenine, 0.002% histidine, 0.002% uracil, 2% agar). The obtained transformant S. cerevisiae (pWI3 pmROL7) was inoculated into an SD-W liquid medium containing 2% casamino acid at an initial glucose concentration of 0.5 to 8.0, and cultured in a Sakaguchi flask to express the lipase gene. The transformant obtained by the culture was disrupted with glass beads, and intracellular lipase was determined by using Lipase Kit S (manufactured by Dainippon Pharmaceutical Co., Ltd.). For comparison, a yeast (Takahashi S. et al., J. Fermentation and Bioengineering 86(2):164–168, 1998) that secretes lipase outside the cell was used (indicated as "secretion type ROL" in Table 3). As a control, a yeast having plasmid pWI3 was used. The results are shown in Table 3.

TABLE 3

| Transformed yeast | Growth ($OD_{600}$) | Intracellular lipase activity (IU/L) | Intracellular lipase specific activity (IU/L) |
|---|---|---|---|
| secretion suppression type pWI3pmROL | 7.49 | 350.6 | 46.81 |
| control pWI3 | 7.59 | 0.00 | 0.00 |
| Secretion type ROL | 16.3 | 10.95 | 0.67 |

Table 3 indicates that the transformant S. cerevisiae (pWI3 pmROL7) accumulates a large amount of lipase within its cell, and the specific activity of the intracellular lipase is about 70 times larger than that of the secretion type.

The obtained transformant S. cerevisiae (pWI3 pmROL7) was cultured in the following manner to produce an immobilized yeast. First, 150 pieces of BSPs with 6 mm cube (manufactured by Bridgestone Corporation) were placed in a 100 ml SD-W liquid medium described above. After the BSPs were sufficiently immersed in the medium, the BSPs were placed in a 500 ml Sakaguchi flask, and 30 g/l of oleic acid was added thereto and the mixture was sterilized in an autoclave at 121° C. for 20 min.

The transformant S. cerevisiae (pWI3 pmROL7) was inoculated into the 100 ml liquid medium that was cooled to 35° C., and was cultured at 30° C. for 24 hours with shaking. After the cultivation, the yeast cells immobilized on the BSPs (hereinafter, referred to as "BSP-immobilized yeast cells") were collected by filtration and washed with water.

The water was removed from the obtained BSP-immobilized yeast cells within an extent that the cells were not removed, and dried at room temperature for 48 hours to obtain intact BSP-immobilized yeast cells.

First, 1 g of water was added to 10 g of a mixture of 9.65 g of soybean oil and 0.35 g of methanol (molar ratio of 1:1) to prepare a reaction mixture. Then, 50 pieces of intact BSP-immobilized yeast cells were added to the reaction mixture, and allowed to react for 20 hours at 30° C. with shaking at 130 rpm. After the reaction, the produced fatty acid ester was quantified by gas chromatography (GC) under the same conditions as in Example 1.

Figure 2:
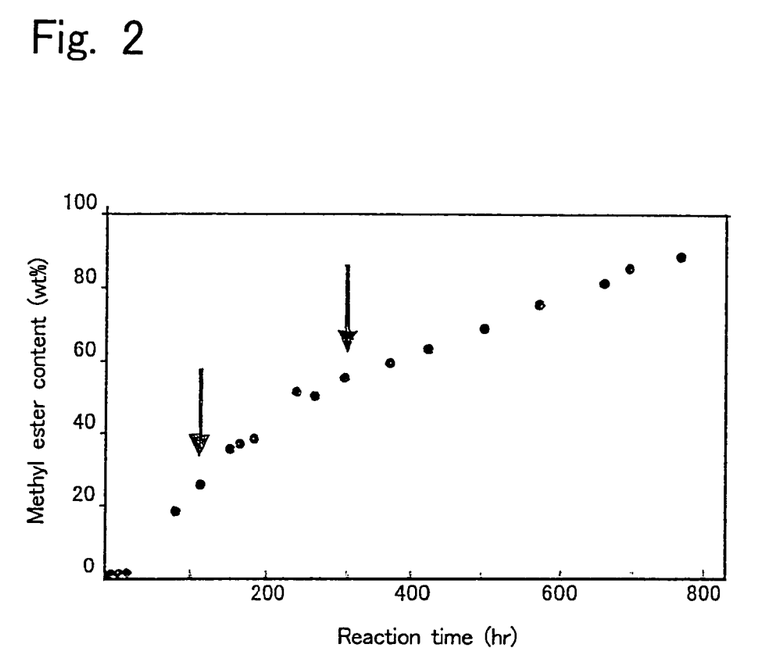
FIG. 2 is a graph showing that a fatty acid ester is produced in the presence of water, by using an intact immobilized yeast having plasmid pWI3pmROL7 and accumulating a lipase within a cell.

The results are shown in FIG. 2. The arrows at 100 hours and 300 hours in FIG. 2 indicate that 0.35 g of methanol was added. The ME content means the content of fatty acid methyl ester.

These results indicate that a fatty acid esterification reaction proceeds sufficiently by using the yeast that expresses lipase within its cell without treating the yeast with any solvent.

Example 4

First, 36.0 g of methanol and 144.0 g of water were mixed with 308.0 g of soybean oil (reaction system A). The molar ratio of the oil and fat and the methanol in the reaction system A is 1:3.2, and the methanol concentration was 20 wt % with respect to the total amount of the methanol and the water. The water content in the reaction system was 29.5%.

On the other hand, for comparison, 68.0 g of methanol and 144.0 g of water were mixed with 308.0 g of soybean oil (reaction system B). The molar ratio of the oil and fat and the methanol in the reaction system B is 1:6, and the methanol concentration was 32 wt % with respect to the total amount of the methanol and the water. The water content in the reaction system was 27.7%.

An esterification reaction was carried out in the following manner. The microorganisms immobilized on the BSPs were filled in the middle state of the column to provide an immobilized microorganism layer, a separating layer is provided under the immobilized microorganism layer. The reaction mixture was removed from the upper portion of the separating layer, and sprayed from the upper portion of the column into the immobilized microorganism layer so that the reaction mixture was circulated. The fatty acid ester was determined in the same manner as in Example 1.

Figure 3:
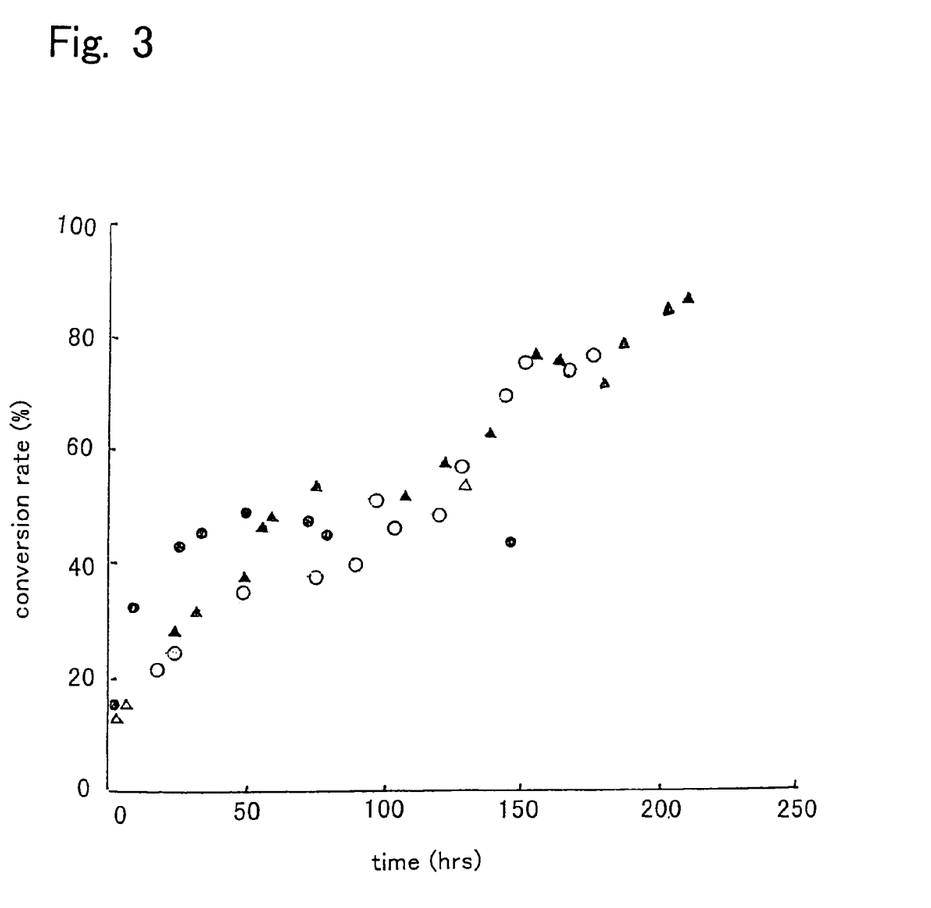
FIG. 3 is a graph showing fatty acid ester synthesis when methanol is contained in a reaction system in ratios of 20 wt % and 32 wt % with respect to the total amount of methanol and water.

The results are shown in FIG. 3. A reaction of the first batch of the reaction system A (▲), a reaction of the second batch of the reaction system A (○), and a reaction of the first batch of the reaction system B (●) are represented in FIG. 3. As seen from FIG. 3, in the reaction system A in which methanol concentration was low, the reaction proceeded substantially 90% or more, and the lipase was not inactivated in the second batch. On the other hand, in the reaction system B in which methanol concentration was 32 wt %, the lipase was inactivated in 50 hours.

Example 5

First, 68.0 g of methanol and 200.0 g of water were mixed with 308.0 g of soybean oil. The molar ratio of the oil and fat and the methanol in the reaction system is 1:6, and the methanol concentration was 25.3 wt % with respect to the total amount of the methanol and the water. The water content in the reaction system was 34.7 wt %. A reaction was carried out using the same apparatus as in Example 4. As a result, unlike in Example 4, the lipase was not inactivated and the reaction proceeded, because the methanol concentration was decreased (the results are not shown).

Example 6

First, 9.24 g (0.3 wt % with respect to soybean oil) of lipase derived from *Candida rugosa* was added to 308.0 g of soybean oil and 144.0 g of water and placed in a water bath at 30° C. with stirring at 110 rpm. Then, 12 g of methanol was added thereto to start a reaction. Methanol was added in an amount of 12 g each after 8 hours and 16 hours. The total amount of the added methanol was 36.0 g, which were eventually 3.2 mols with respect to one mol of the soybean oil. The fatty acid ester was determined in the same manner in Example 1. The experiments were conducted twice, and the yields of the fatty acid ester at 24 hours after were 85% and 91%, respectively.

INDUSTRIAL APPLICABILITY

The method for synthesizing an ester according to the present invention is carried out in a system containing no solvent and in the presence of water, using a lipase or a microorganism without any treatment, so that the operation is simple, and an ester is synthesized efficiently. In particular, the present invention makes it possible to utilize waste oils containing a large amount of water, and to recycle the waste oil to be dumped into the environment. At the same time, the present invention provides a biodiesel fuel, which hardly pollutes the environment.

Furthermore, it is unnecessary to isolate an enzyme, so that the process required for purification of the enzyme and the cost can be eliminated, which leads to simplification of the process and reduction of the cost. Moreover, conventionally used solvents for treatment of microorganisms and reaction can be eliminated, and the consequently required facilities for collection of the solvents, prevention of explosion and the like also can be eliminated, which can reduce the cost significantly.

What is claimed is:

1. A method for producing a fatty acid ester comprising reacting an intact microorganism containing a lipase within the microorganism with an oil and fat and a linear lower alcohol in a system containing little or no solvent in which water is contained in an amount of 0.3 wt % or more in a reaction mixture.

2. The method of claim 1, wherein the intact microorganism is immobilized on a porous support.

3. The method of claim 1, wherein the microorganism can accumulate within the microorganism a recombinant lipase that does not have a functional sequence involved in secretion.

4. The method of claim 1, wherein the oil and fat is a vegetable oil and fat, an animal oil and fat, a fish oil, an oil and fat produced by a microorganism, a mixture of these oils and fats, or a waste oil thereof.

5. The method of claim 1, wherein the linear lower alcohol is methanol, which is adjusted so that it is contained in an amount of 30 wt % or less with respect to a total amount of the methanol and the water.

6. The method of claim 1, wherein the linear lower alcohol is added stepwise.

* * * * *